United States Patent
Christensen, IV et al.

(10) Patent No.: US 6,670,394 B1
(45) Date of Patent: Dec. 30, 2003

(54) METHOD FOR TREATING COPD

(75) Inventors: Siegfried B. Christensen, IV, Philadelphia, PA (US); Mary S. Barnette, West Chester, PA (US); Theodore J. Torphy, Bryn Mawr, PA (US)

(73) Assignee: SmithKline Beecham Corporation, Philadelphia, PA (US)

( * ) Notice: Subject to any disclaimer, the term of this patent is extended or adjusted under 35 U.S.C. 154(b) by 0 days.

(21) Appl. No.: 09/914,703

(22) PCT Filed: Mar. 1, 2000

(86) PCT No.: PCT/US00/05227

§ 371 (c)(1),
(2), (4) Date: Aug. 31, 2001

(87) PCT Pub. No.: WO00/51598

PCT Pub. Date: Sep. 8, 2000

Related U.S. Application Data

(60) Provisional application No. 60/122,315, filed on Mar. 1, 1999.

(51) Int. Cl.[7] ............... A61K 31/165; A61K 31/192; A61K 31/216; A61K 31/30

(52) U.S. Cl. ............... 514/520; 514/362; 514/363; 514/364; 514/381; 514/382; 514/521; 514/522; 514/530; 514/531; 514/538; 514/567; 514/615; 514/619; 514/646; 514/826; 514/851; 514/885

(58) Field of Search ............... 514/362, 363, 514/364, 381, 382, 520, 530, 531, 538, 521, 522, 567, 615, 619, 646, 826, 851, 885

(56) References Cited

U.S. PATENT DOCUMENTS

| | | | | |
|---|---|---|---|---|
| 5,552,438 A | * | 9/1996 | Christensen, IV et al. | 514/520 |
| 5,605,923 A | * | 2/1997 | Christensen, IV et al. | 514/417 |
| 6,143,782 A | | 11/2000 | Barnette et al. | 514/521 |
| 6,369,108 B1 | | 4/2002 | Christensen et al. | 514/567 |

\* cited by examiner

*Primary Examiner*—Frederick Krass
(74) *Attorney, Agent, or Firm*—James M. Kanagy; Stephen Venetianer; Charles M. Kinzig

(57) ABSTRACT

This invention relates to a method for the prophylaxis of or for treating COPD by administering a PDE4 inhibitor which has a defined therapeutic ratio.

4 Claims, No Drawings

METHOD FOR TREATING COPD

This application is a §371 of PCT/US00/05007, filed Mar. 1, 2000, and claims the benefit of priority of U.S. Provisional Application No. 60/122,315, filed Mat. 1, 1999.

SCOPE OF THE INVENTION

This invention covers compounds which preferentially inhibit, or bind, one form of a phosphodiesterase isozyme denominated 4 (PDE 4 hereafter) while exhibiting equal or, preferably less binding or inhibition for a second form of the enzyme and are thus useful for treating chronic obstructive pulmonary disease (COPD). These isoenzyme forms, and it is believed they are different forms of non-interconvertible conformations of the same enzyme though this has not been proven, are distinguished by their binding affinity for rolipram, an architypical PDE 4 inhibitor. Rolipram binds with high affinity to a site of one form but with low affinity to the catalytic site of the other. Herein one form is denominated the high affinity rolipram binding site and the other form is identified as the low affinity rolipram binding site. A method for selectively treating chronic obstructive pulmonary disease by inhibiting preferentially the low affinity form of the catalytic site in the PDE 4 isozyme is also disclosed. A method for treating COPD comprising administering a compound preferentially binding to the low affinity binding site is also disclosed. A method for selectively treating exercise induced asthma (EIA) by inhibiting preferentially the low affinity form of the catalytic site in the PDE 4 isozyine is also disclosed.

BACKGROUND OF THE INVENTION

Cyclic nucleotide phosphodiesterases (PDEs) represent a family of enzymes that hydrolyze the ubiquitous intracellular second messengers, adenosine 3',5'-monophosphate (cAMP) and guanosine 3',5'-monophosphate (cGMP) to their corresponding inactive 5'-monophosphate metabolites. At least nine distinct classes of PDE isozymes are believed to exist, each possessing unique physical and kinetic characteristics and each representing a product of a different gene family. These have been distinguished using the numerals 1 through 9.

The target enzyme in this invention is the PDE 4 isozyme in all its various forms and in the full domain of its distributions in all cells. It is a low $K_m$ (cAMP $K_m$=1–5 $\mu M$) cAMP-selective enzyme that has little activity against cGMP (Km>100 $\mu M$). Members of this isozyme class have the interesting characteristics of existing in two or more non-interconvertible or slowly interconvertible forms that bind rolipram and other PDE 4 inhibitors with distinct rank order potencies. Thus the same gene product can exist in more than one catalytically active conformational state. Importantly, the relative proportions of the different binding forms may vary depending on the tissue cell type. For example, inflammatory cells may contain a relatively high proportion of the form that binds rolipram with a low affinity while brain and parietal cells may contain a relatively high proportion of the form that binds rolipram with a high affinity.

Of particular interest in this invention is the role this class of isozymes play in inflammation and airway smooth muscle. Studies indicate that it plays a prominent role in regulating cAMP in a wide variety of inflammatory cells (i.e., mast cells. basophils, eosinophils, neutrophils, and monocytes) and airway smooth muscle. The work of this invention is particularly applicable to inflammatory cells and airway smooth muscle; the isozyme type expressed in human monocytes is of particular interest. This is because cyclic AMP serves as a second messenger to inhibit chemotaxis and activation of inflammatory cells. In addition, cAMP mediates smooth airway muscle relaxation. This coupled with the major role of PDE 4 in metabolizing cAMP has provided the underpinnings for investigating PDE 4 inhibitors: by virtue of their ability to elevate cAMP content in leukocytes and airway smooth muscle, PDE 4 inhibitors may posses anti-inflammatory and bronchodilator activities.

Current PDE inhibitors used in treating inflammation and as bronchodilators, drugs like theophylline and pentoxyfyllin, inhibit PDE isozymes indiscriminently in all tissues These compounds exhibit side effects, apparently because they non-selectively inhibit all or most PDE isozyme classes in all tissues. This is a consideration in assessing the therapeutic profile of these compounds. The targeted disease state may be effectively treated by such compounds, but unwanted secondary effects may be exhibited which, if they could be avoided or minimized, would increase the overall therapeutic effect of this approach to treating certain disease states. Taken collectively, this information suggests that the side effects associated with the use of standard non-selective PDE inhibitors might be reduced by targeting novel isozyme-selective inhibitors for the predominant PDE in the tissue or cell of interest. Although in theory isozyme-selective PDE inhibitors should represent an improvement over non-selective inhibitors, the selective inhibitors tested to date are not devoid of side effects produced as an extension of inhibiting the isozyme of interest in an inappropriate or not-targeted tissue. For example, clinical studies with the selective PDE 4 inhibitor rolipram, which was being developed as an antidepressant, indicate it has psychotropic activity and produces gastrointestinal effects, e.g., pyrosis, nausea and emesis. Indications are that side effects of denbufylline, another PDE 4 inhibitor targeted for the treatment of multi-infarct dementia, may include pyrosis, nausea and emesis as well. These side effects are thought to occur as a result of inhibiting PDE 4 in specific areas of the CNS and gastrointestinal system.

In 1986, Schneider and colleagues described the presence and characteristics of high affinity, stereoselective [$^3$H]-rolipram binding sites in rat brain homogenates. Although it was assumed that these binding sites represented the catalytic site of the rat brain "non-calmodulin-dependent, cAMP phosphodiesterase" (i.e. PDE 4), a striking anomaly was apparent in the data. Under similar albeit not identical experimental conditions, data showed rolipram had a $K_d$=1 nM, whereas it inhibited rat brain PDE 4 activity with a $K_i$=1 $\mu M$. Thus, there was a 1000-fold difference in the affinity of rolipram for the binding site versus its affect on catalytic activity. Although comprehensive structure activity relationships (SARs) for PDE inhibition and competition for [$^3$H]-rolipram binding were not established, the substantial difference in the potency of rolipram as a PDE 4 inhibitor compared with its potency at the binding site seemed to question the validity of the assumption that both activities were contained within the same molecular locus.

Because of this conundrum, several studies were initiated. One sought to determine whether rolipram's high affinity binding site existed on the same protein as the cAMP catalytic site. Another study sought to determine whether or not the SAR for inhibition of PDE 4 was the same as the SAR for competition with the high affinity rolipram binding site. A third study undertook to try and elucidate what biological significance, if any, there might be in these findings, particularly as it might relate to developing new drug therapies.

As data were collected from several assays, it became apparent that there are at least two binding forms on human monocyte recombinant PDE 4 (hPDE 4) at which inhibitors bind. One explanation for these observations is that hPDE 4 exists in two distinct forms. One binds the likes of rolipram and denbufylline with a high affinity while the other binds these compounds with a low affinity. Herein we distinguish these forms by referring to them as the high affinity rolipram binding form (HPDE 4) and the low affinity rolipram binding form (LPDE 4).

The importance of this finding lies in the discovery that compounds which potently compete for the high affinity rolipram binding form (HPDE 4) have more side effects or more intense side effects than those which more potently compete with the LPDE 4 (low affinity rolipram binding form). Further data indicate that compounds can be targeted to the low affinity binding form of PDE 4 and that this form is distinct from the binding form for which rolipram is a high affinity binder. Distinct SARs were found to exist for inhibitors acting at the high affinity rolipram binding form versus the low affinity rolipram binding form. In addition, these two forms appear to have different functional roles. Thus compounds that interacted with the low affinity rolipram binding form appear to have anti-inflammatory activity, whereas those that interact with the high affinity rolipram binding form produce side effects or exhibit more intensely those side effects.

There is no clear explanation for these findings. However, it is proposed the PDE 4 can exist in two distinct tertiary or quaternary states. Both forms are believed to be catalytically active. Rolipram binds to one catalytic site of one form with a high affinity, defined herein as having a $K_i$ less than 10 nanomolar, and to the other form with a low affinity, defined here as having a $K_i$ of greater than 100 nanomolar.

A useful consequence of these findings is that it is now possible to identify compounds which preferentially inhibit cAMP catalytic activity where the enzyme is in the form that binds rolipram with a low affinity, thereby reducing the side effects which apparently are linked to inhibiting the form which binds rolipram with a high affinity.

Chronic obstructive pulmonary disease (COPD) is an umbrella term frequently used to describe two conditions of fixed airways disease, chronic bronchitis and emphysema. Chronic bronchitis and emphysema are most commonly caused by smoking; approximately 90% of patients with COPD are or were smokers. Although approximately 50% of smokers develop chronic bronchitis, only 15% of smokers develop disabling airflow obstruction. Certain other mammals, particularly horses, suffer from COPD as well.

The airflow obstruction associated with COPD is progressive,.may be accompanied by airway hyperreactivity, and may be partially reversible. Non-specific airway hyper-responsiveness may also play a role in the development of COPD and may be predictive of an accelerated rate of decline in lung function in smokers.

COPD is a significant cause of death and disability. It is currently the fourth leading cause of death in the United States and Europe. Treatment guidelines advocate early detection and implementation of smoking cessation programs to help reduce morbidity and mortality due to the disease. However, early detection and diagnosis has been difficult for a number of reasons.

COPD takes years to develop and smokers often deny any ill effects from smoking, attributing the early warning signs of increased breathlessness as a sign of age. Similarly, acute episodes of bronchitis often are not recognized by the general practitioner as early signs of COPD. Many patients exhibit features of more than one disease (e.g. chronic bronchitis or asthmatic bronchitis) making precise diagnosis a challenge, particularly in early disease. Also, many patients do not seek medical help until they are experiencing more severe symptoms associated with reduced lung function, such as dyspnea, persistent cough, and sputum production. As a consequence, the vast majority of patients are not diagnosed or treated until they are in a more advanced stage of disease.

This invention thus provides a superior therapeutic index vis-à-vis COPD versus side effects.

SUMMARY OF THE INVENTION

This invention relates to a method for the prophylaxis of or treating COPD while minimizing gastrointestinal and psychotropic effects, which method comprises administering to a subject in need thereof an effective amount of a compound having an $IC_{50}$ ratio of about 0.1 or greater as regards the $IC_{50}$ for PDE 4 catalytic form which binds rolipram with a high affinity divided by the $IC_{50}$ for the form which binds rolipram with a low affinity.

DETAILED DESCRIPTION OF THE INVENTION

COPD is characterized by a chronic inflammatory process in the lung marked by in increase in the activation and/or number of alveolar macrophages, $CD8^+$T-cells and neutrophils. Most notably with respect to the therapy of COPD is the ability to alter the trafficking and activation of neutrophils. The neutrophil is believed to play a central role in the pathophysiology of COPD. Neutrophil activation results in the release of a number of inflammatory mediators and proteinases, most importantly neutrophil elastase which contributes to the progressive fibrosis, airway stenosis and destruction of the lung parenchyma, leading to an accelerated decline in airway function. Neutrophil elastase is also a powerful mucus secretagogue and thus may contribute to the characteristic mucus hypersecretion that characterizes COPD. The compounds of this invention have marked effects on neutrophil activity, inhibiting neutrophil chemotaxis and degranulation in vitro. In animal models, the instant compounds reduce neutrophil extravasation from the circulation, pulmonary sequestration and the edematous responses to a number inflammatory insults in vivo.

Additional activities that may contribute to the therapeutic activity of PDE4 inhibitors in COPD include bronchodilation and modulation of pulmonary neuronal activity. Although the degree of reversibility of reduced airway flow is low in COPD, a small increase may have an acute positive effect, as well as a gradual reduction in the slope of the decline which may result in a profound effect on quality of life for COPD patients. The ability of inhaled muscarinc antagonists to produce clinically meaningful improvements in pulmonary function in COPD, at least acutely, suggest that a large component of the reversible airways obstruction in this disease is associated with a dysregulation of pulmonary nerves. Although not studied in detail as yet, PDE4 inhibitors may also modulate the activity of airway epithelial cells, a rich source of proinflammatory mediators that are released upon environmental insult (e.g., smoke), and inhibit vascular smooth muscle hyperplasia, a structural change in end stage COPD that is associated with right heart failure.

For purposes of this invention, the cAMP catalytic site which binds rolipram with a low affinity is denominated the "low affinity" binding site (LPDE 4) and the other form of this catalytic site which binds rolipram with a high affinity is denominated the "high affinity" binding site (HPDE 4).

Initial experiments were conducted to establish and validate a [3H]-rolipram binding assay. Details of this work are given in Example 1 below.

To determine whether both the high affinity binding activity and the low affinity binding activity resided in the same gene product, yeast were transformed by known methods and the expression of recombinant PDE 4 was followed over a 6 hour fermentation period. Western blot analysis using an antibody directed against PDE 4 indicated that the amount of PDE 4 expressed increased with time, reaching a maximum after 3 hour of growth. In addition, greater than 90% of the immunoreactive product was in the high speed (100,000×g) supernatant of yeast lysates. [$^3$H]R-(-)-Rolipram binding and PDE activity were monitored along with protein expression. PDE 4 activity was co-expressed with rolipram binding activity, indicating that both functions exist on the same gene product. Similar to results with the Western plot analysis, greater than 85% of the rolipram-inhibitable PDE activity and [$^3$H]-rolipram binding activity was found to be present in the yeast supernatant fraction.

Overall, most of the recombinant PDE 4 expressed in this system exists as LPDE 4 and only a small fraction as HPDE 4. Consequently, inhibition of recombinant PDE 4 catalytic activity primarily reflects the actions of compounds at LPDE 4. Inhibition of PDE 4 catalytic activity can thus be used as an index of the potency of compounds at LPDE 4. The potency of compounds at HPDE 4 can be assessed by examining their ability to compete for [$^3$H]R-(-)-rolipram. To develop structure-activity relationships (SARs) for both the low affinity and high affinity rolipram binding sites, the potencies of selected compounds were determined in two assay systems. Results from experiments using standard compounds were tabulated. As expected, certain compounds were clearly more potent in competing with [$^3$H]-rolipram at the site for which rolipram demonstrated high affinity binding as compared with the other site, the one at which rolipram is a low affinity binder. SAR correlation between high affinity binding and low affinity binding was poor and it was concluded that the SAR for inhibition of high affinity [$^3$H]-rolipram binding was distinct from the SAR for binding to the low affinity rolipram binding site. Table I provides results from this SAR work.

TABLE I

| Compound | Low Affinity IC$_{50}$ | High Affinity IC$_{50}$ | High/Low Ratio |
| --- | --- | --- | --- |
| 1-(5-tetrazole)-3-(3-cyclopentyloxy-4-methoxyphenyl)cyclopentane | 1.1 | 0.002 | 0.0018 |
| cis-[3-(3-cyclopentyloxy-4-methoxyphenyl)cyclopentane-1-carboxylate] | 2.7 | 0.021 | 0.0078 |
| N-[2-(3-cyclopentyloxy-4-methoxyphenyl)ethyl]oxamide | 0.89 | 0.012 | 0.013 |
| R-rolipram | 0.31 | 0.004 | 0.013 |
| N-[2-(3,4-bisdifluoromethoxy-phenyl)ethyl]oxamide | 1.6 | 0.4 | 0.25 |
| Ro 20-1724 | 2.6 | 0.19 | 0.07 |
| S-rolipram | 1.1 | 0.095 | 0.086 |
| (R)-(+)-1-(4-bromobenzyl)-4-[(3-cyclopentyloxy)-4-methoxyphenyl]-2-pyrrolidone | 4.0 | 0.45 | 0.11 |
| 1-(4-aminobenzyl)-4-(3-cyclopentyloxy-4-methoxyphenyl)-2-imidazolidinone | 1.4 | 0.1 | 0.07 |
| denbufylline | 0.29 | 0.05 | 0.17 |
| 3-(cyclopentyloxy-4-methoxyphenyl)-1-(4- | 0.1 | 0.03 | 0.30 |

TABLE I-continued

| Compound | Low Affinity IC$_{50}$ | High Affinity IC$_{50}$ | High/Low Ratio |
| --- | --- | --- | --- |
| N'-[N2-cyano-S-methyl-isothioureido]benzyl)-2-pyrrolidone (R)-(+)-1-(4-bromobenzyl)-4-[(3-cyclopentyloxy)-4-methoxyphenyl]-2-pyrrolidone | 0.06 | 0.02 | 0.33 |
| IBMX | 29.1 | 20.3 | 0.698 |
| (S)-(-)-ethyl[4-(3-cyclopentyloxy-4-methoxyphenyl)pyrrolidine-2-ylidene]acetate | 0.46 | 0.45 | .98 |
| Papaverine | 10 | 10 | 1.0 |
| cis-[4-cyano-4-(3-cyclopentyloxy-4-methoxyphenyl)cyclohexan-1-carboxylate] | 0.095 | 0.110 | 1.1 |
| cis-[4-cyano-4-(3-cyclopropylmethoxy-4-difluoromethoxyphenyl)cyclohexan-1-ol] | 0.021 | 0.04 | 2.0 |
| (R)-(+)-ethyl [4-(3-cyclopentyloxy-4-methoxyphenyl)pyrrolidine-2-ylidene]acetate | 0.14 | 0.3 | 2.143 |
| 2-carbomethoxy-4-cyano-4-(3-cyclopropylmethoxy-4-difluoromethoxyphenyl)cyclohexan-1-one | 0.140 | 0.5 | 3.571 |
| trequinsin | 1.6 | 5.0 | 3.125 |
| dipyridamole | 5.2 | 32.5 | 6.25 |

Denbufylline is 7-acetonyl, 1,3-dibutylxanthine made by SmithKline Beecham. Papaverine is 1-[(3,4-dimethoxyphenyl)methyl]-6,7-dimethoxyisoquinoline. Trequinsin is 2,3,6,7-tetrahydro-2-(mesitylimino)-9,10-dimethoxy-3-methyl-4H-primido[6,1-a]isoquinoline-4-one. Dipyrimadole is the generic name for 2,2',2",2'''-[(4,8-dipiperidinopyrimido[5,4-d]pyrimidine-2-6-diylidinitrilo] tetraethanol.

These results illustrate that some compounds can selectively inhibit the so called low affinity form as compared with the high affinity form, and vice versa. The significance of this finding is that it is feasible to minimize side effects by designing or choosing compounds which selectively (preferentially) inhibit one site thereby affecting the desired response to the exclusion of another, unwanted, response, or at least to minimize the non-targeted response to a degree where it is not interfering with the intended therapy to an unacceptable degree.

Notwithstanding this work, we have not defined the basis for the disparate SARs for high affinity rolipram binding and low affinity rolipram binding in the PDE 4 isozyme,. However it has been discovered that if a compound exhibits an IC$_{50}$ ratio of about 0.1 or greater, calculated as the ratio of the IC$_{50}$ for high affinity rolipram binding form divided by the IC$_{50}$ for the form which binds rolipram with a low affinity, it will have an acceptable therapeutic index. That is, one can now successfully treat a variety of immune and inflammatory diseases while not affecting other physiological phenomena at all or to an unacceptable degree. Herein the most preferred embodiment is inhibiting the low affinity rolipram binding site as a means for treating inflammatory and allergic diseases.

Compounds

This invention covers those compounds which have an IC$_{50}$ ratio (high/low binding) of about 0.1 or greater. This includes any and all compounds which are PDE 4 inhibitors as per the test set our herein, and which demonstrate in these, or similar assays, a ratio within the defined range; of particular interest are those compounds which are not in the public domain and/or not tested as or known to be PDE 4 inhibitors prior to the filing date of this application.

A preferred technique for selecting useful compounds is that of determining one having an IC$_{50}$ ratio of about 0.1 or greater ratio of the $IC_{50}$ value for competing with the binding of 1 nM of [$^3$H]R-rolipram to a form of PDE 4 which binds rolipram with a high affinity over the $IC_{50}$ value for inhibiting the PDE 4 catalytic activity of a form which binds rolipram with a low affinity using 1 $\mu$M[$^3$H]-cAMP as the substrate.

Examples of compounds which meet the $IC_{50}$ ratio standard are given in Table 1 above as well as U.S. Pat. No. 5,448,686; U.S. Pat. No. 5,605,923; and U.S. Pat. No. 5,552,438. Each of these applications is incorporated herein by reference in full as if set out in this document.

Preferred compounds of this invention are those which have an $IC_{50}$ ratio of greater than 0.5; and particularly those compounds having a ratio of greater than 1.0. Compounds such as cis-[4-cyano-4-(3-cyclopentyloxy-4-methoxyphenyl)cyclohexan-1-carboxylate], 2-carbomethoxy-4-cyano-4-(3-cyclopropylmethoxy-4-difluoromethoxyphenyl)cyclohexan-1-one, and cis-[4-cyano-4-(3-cyclopropyimethoxy-4-difluoromethoxyphenyl) cyclohexan-1-ol] are examples of structures which bind preferentially to the low affinity binding site and which have an $IC_{50}$ ratio of 0.1 or greater.

The present compounds and pharmaceutically acceptable salts may be administered in a standard manner for the treatment of the indicated diseases, for example orally, parenterally, sub-lingually, dermally, transdermally, rectally, via inhalation or via buccal administration. A controlled-release preparation can also be utilized.

The present compounds and pharmaceutically acceptable salts which are active when given orally can be formulated as syrups, tablets, capsules, controlled-release preparation or lozenges. A syrup formulation will generally consist of a suspension or solution of the compound or salt in a liquid carrier for example, ethanol, peanut oil, olive oil, glycerine or water with a flavoring or coloring agent. Where the composition is in the form of a tablet, any pharmaceutical carrier routinely used for preparing solid formulations may be used. Examples of such carriers include magnesium stearate, terra alba, talc, gelatin, acacia, stearic acid, starch, lactose and sucrose. Where the composition is in the form of a capsule, any routine encapsulation is suitable, for example using the aforementioned carriers in a hard gelatin capsule shell. Where the composition is in the form of a soft gelatin shell capsule any pharmaceutical carrier routinely used for preparing dispersions or suspensions may be considered, for example aqueous gums, celluloses, silicates or oils, and are incorporated in a soft gelatin capsule shell.

Typical parenteral compositions consist of a solution or suspension of a compound or salt in a sterile aqueous or non-aqueous carrier optionally containing a parenterally acceptable oil, for example polyethylene glycol, polyvinylpyrrolidone, lecithin, arachis oil or sesame oil.

Typical compositions for inhalation are in the form of a solution, suspension or emulsion that may be administered as a dry powder or in the form of an aerosol using a conventional propellant such as dichlorodifluoromethane or trichlorofluoromethane.

Typical dermal and transdermal formulations comprise a conventional aqueous or non-aqueous vehicle, for example a cream, ointment, lotion or paste or are in the form of a medicated plaster, patch or membrane.

Preferably the composition is in unit dosage form, for example a tablet, capsule or metered aerosol dose, so that the patient may administer a single dose.

Each dosage unit for oral administration contains suitably from 0.3 mg to 60 mg/Kg, and preferably from 1 mg to 30 mg/Kg of a compound or a pharmaceutically acceptable salt thereof. Preferred doses include 10 mg and 15 mg/Kg for treating COPD. Each dosage unit for parenteral administration contains suitably from 0.1 mg to 100 mg/Kg, of the compound or a pharmaceutically acceptable salt thereof. Each dosage unit for intranasal administration contains suitably 1–400 mg and preferably 10 to 200 mg per person. A topical formulation contains suitably 0.01 to 5.0% of a present compound.

The active ingredient may be administered from 1 to 6 times a day, sufficient to exhibit the desired activity. Preferably, the active ingredient is administered about once or twice a day, more preferably twice a day.

No unacceptable toxicological effects are expected when compounds of the present invention are administered in accordance with the present invention.

The following examples are provided to illustrate how to make and use the invention. They are not in any way intended to limit the scope of the invention in any manner or to any degree. Please refer to the claims for what is reserved to the inventors hereunder.

EXAMPLES

The following eight assays spread among five species were used to develop data supporting the selection of an $IC_{50}$ ratio of about 0.1 or greater. The assays were: stimulation of acid production from rabbit isolated parietal gland; inhibition of FMLP-induced degranulation (release of myleoperoxidase) in human neutrophils; inhibition of FMLP-included $O_2^-$ formation in guinea pig eosinophils; inhibition of LPS-induced TNF$\alpha$ production in human monocytes; production of emesis in dogs; inhibition of antigen-induced bronchoconstriction in guinea pigs; reversal of reserpine-induced hypothermia in mice; and inhibition of LPS-induced TNF$\alpha$ production from adoptively-transferred human monocytes in mice. These assays and data are presented below.

Statistical Analysis

To examine the hypothesis that inhibition of the low affinity site PDE 4 is associated with the anti-inflammatory actions of this class of compounds, whereas inhibition of the high affinity site is associated with the production of certain side effects, we determined the ability of various PDE 4 inhibitors to block inflammatory cell function both in vitro and in vivo and the ability of these compounds to produce side effects in in vitro and in vivo models. To compare the ability of PDE 4 inhibitors to elicit a given therapeutic effect or side effect with their ability to inhibit the low affinity binding site versus their ability to inhibit the high affinity site of PDE 4, we compared the potency of these compounds in the in vitro or in vivo assays with their potency against the isolated enzyme catalytic activity or the high affinity site by a linear correlation of ($r^2$) or a rank order correlation (Spearman's Rho). The linea correlation asks whether the potency of a compound at inhibiting either the low affinity site or the high affinity site can be used to predict the ability to elicit a given anti-inflammatory or side effect. The rank order correlation tests whether the rank order potency in producing a given anti-inflammatory or side effect is similar to the rank order potency in inhibiting the low affinity or the high affinity site. Both $r^2$ and Spearman's Rho were calculated using the STAT View II computer program for the Macintosh.

PDE 4 Versus Rolipram High Affinity Binding

Example 1—Phosphodiesterase and Rolipram Binding Assays

Example 1A

Isolated human monocyte PDE 4 and hrPDE (human recombinant PDE4) was determined to exist primarily in the low affinity form. Hence, the activity of test compounds against the low affinity form of PDE 4 can be assessed using standard assays for PDE 4 catalytic activity employing 1 μM [$^3$H]cAMP as a substrate (Torphy et al., *J. of Biol. Chem.*, Vol. 267, No. 3 pp1798–1804, 1992).

Rat brain high speed supernatants were used as a source of protein. Enantionmers of [$^3$H]-rolipram were prepared to a specific activity of 25.6 Ci/mmol. Standard assay conditions were modified from the published procedure to be identical to the PDE assay conditions, except for the last of the cAMP: 50 mM Tris HCl (pH 7.5), 5 mM MgCl$_2$, and 1 nanoM of [$^3$H]-rolipram (Torphy et al., *J. of Biol. Chem.*, Vol. 267, No. 3 pp1798–1804, 1992). The assay was run for 1 hour at 30° C. The reaction was terminated and bound ligand was separated from free ligand using a Brandel cell harvester. Competition for the high affinity binding site was assessed under conditions that were identical to those used for measuring low affinity PDE activity, expect that [$^3$H]-cAMP and [$^3$H]5'-AMP were not present. The data presented in Table 1, page 8 were generated using the protocol described in Example 1A.

Example 1B

Measurement of Phosphodiesterase Activity

PDE activity was assayed using a [$^3$H]cAMP scintillation proximity assay (SPA) or [$^3$H]cGMP SPA enzyme assay as described by the supplier (Amersham Life Sciences). The reactions were conducted in 96-well plates at room temperature, in 0.1 ml of reaction buffer containing (final concentrations): 50 mM Tris-HCl, pH 7.5, 8.3 mM MgCl2, 1.7 mM EGTA, [$^3$H]cAMP or [$^3$H]cGMP (approximately 2000 dpm/pmol), enzyme and various concentrations of the inhibitors. The assay was allowed to proceed for 1 hr and was terminated by adding 50 μl of SPA yttrium silicate beads in the presence of zinc sulfate. The plates were shaken and allowed to stand at room temperature for 20 min. Radiolabeled product formation was assessed by scintillation spectrometry. Activities of PDE3 and PDE7 were assessed using 0.05 μM [$^3$H]cAMP, whereas PDE4 was assessed using 1 μM [$^3$H]cAMP as a substrate. Activity of PDE1B, PDE1C, PDE2 and PDE5 activities were assessed using 1 μM [$^3$H]cGMP as a substrate.

[$^3$H]R-rolipram Binding Assay

The [$^3$H]R-rolipram binding assay was performed by modification of the method of Schneider and co-workers, see Nicholson, et al., *Trends Pharmacol. Sci.*, Vol. 12, pp.19–27 (1991) and McHale et al., *Mol. Pharmacol.*, Vol. 39, 109–113 (1991). R-rolipram binds to the catalytic site of PDE4 see Torphy et al., *Mol. Pharmacol.*, Vol. 39, pp. 376–384 (1991). Consequently, competition for [$^3$H]R-rolipram binding provides an independent confirmation of the PDE4 inhibitor potencies of unlabeled competitors. The assay was performed at 30° C. for 1 hr in 0.5 μl buffer containing (final concentrations): 50 mM Tris-HCl, pH 7.5, 5 mM MgCl$_2$, 0.05% bovine serum albumin, 2 nM [$^3$H]R-rolipram (5.7×104 dpm/pmol) and various concentrations of non-radiolabeled inhibitors. The reaction was stopped by the addition of 2.5 ml of ice-cold reaction buffer (without [$^3$H]-R-rolipram) and rapid vacuum filtration (Brandel Cell Harvester) through Whatman GF/B filters that had been soaked in 0.3% polyethylenimine. The filters were washed with an additional 7.5-ml of cold buffer, dried, and counted via liquid scintillation spectrometry.

Example 2—Aminopyrine Accumulation

Certain methylxanthines and other non-selective PDE inhibitors increase acid secretion in a variety of species. Certain selective PDE 4 inhibitors, e.g., rolipram and Ro 20-1724, enhance acid secretion in rats, particularly when given in combination with an activator of adenylate cyclase such as histamine. This increase in acid secretion is accompanied by an elevation of histamine-induced cAMP accumulation. This reported information was tested to determine if the phenomena existed. The ability of compounds to induce acid secretion was correlated with their ability against the low affinity site or the high affinity site. The assay used in this work was the accumulation of a weak base, radiolabeled aminopyrine which has been reported to serve as a biochemical marker for increased acid secretion. The assay follows:

Gastric Gland Preparation

Rabbits of either sex were euthanized by cervical dislocation and the stomach removed. The mucosa was dissected from the corpus; the cranial and antral portions of the stomach were discarded. Gastric glands were isolated by a modification of the methods described by Berglindh and Obrink (1976) and Sack and Spenney (1982). The mucosa was then minced and digested with collagenase to isolate the gastric glands. The digested glands were filtered, washed, and resuspended 1:15 (vol:vol) in incubation medium of the following composition: NaCl, 132.4 mM; KCl, 5.4 mM; Na$_2$HPO$_4$, 5.0 mM; NaH$_2$PO$_4$, 1.0 mM; MgSO$_4$, 1.2 mM; CaCl$_2$, 1.0 mM; NaHCO$_3$, 12.0 mM; rabbit serum albumin, 2 mg/ml; dextrose, 2 mg/ml; at a pH 7.4.

Aminopyrine Accumulation

To determine acid secretion, the gastric glands in combination with [$^{14}$C]-aminopyrine, various concentrations of selective PDE 4 inhibitors, and a threshold concentration of histamine (0.3–1.0 μM) were incubated at 37° C. on a horizontal shaker (110 cycles/min) for 20 minutes according to the procedures of Sack and Spinney (1982). Samples were then centrifuged and radioactivity in aliquots of the supernatant fraction and pellet were determined. Aminopyrine ratios were calculated as described by Sack and Spenney (1982). The data were expressed as a percent of a response produced by a maximal concentration of histamine (100 μM). EC$_{50}$ values were determined by linear interpolation using the maximum response obtained for each compound.

Example 3—Evaluation of the Emetic Potential of Selective PDE Inhibitors in Dogs Mongrel dogs (n=5, for each study) of either sex were obtained from the animal colony. After an overnight fast, the dogs were fed ½ can of dog food (Big Bet) at least 30 minutes prior to study. A cannula was placed in the cephalic vein of either foreleg to administer drugs. The cannula was flushed with 1 ml of isotonic saline (0.9%) prior to administration of the experimental compound. Compounds were dissolved in either a mixture of polyethylene glycol and saline or 100% polyethylene glycol and given at a volume of 1.0–2.0 ml/10 kg. To insure that the entire dose entered the circulation, the cannula was flushed with additional 0.5–1.0 ml of saline. The animal was returned to a cage for a 1 hour observation period. Each dog was observed for signs of retching or vomiting and the time after administration of compound for the occurrence of this behavior was noted. At the end of the observation period, the animal was returned to its home cage. Each study day was separated by 7 days. Each compound was administered in ascending doses to each dog on successive study days until an emetic effect was observed. At this time, the individual dog was dropped from the study and higher doses were evaluated in only those dogs that had not yet responded.

The data were expressed as the cumulative percent of dogs responding at each dose as described in the literature for quantal dose response curves. An $ED_{50}$ value was calculated using probit analysis.

Example 4—Guinea Pig Eosinophil Assay

Eosinophil Isolation and Purification

Male (Hartley, Hazelton Labs) guinea pigs were injected with 1 ml of horse serum weekly for 4–6 weeks prior to use. Animals were anesthetized with a mixture of ketamine/xylazine (88 mg; 12 mg/ml; 0.4 ml/kg at least 24 hrs after an injection of horse serum. After the induction of anesthesia the peritoneal cavity was lavaged with 50 ml of warm sterile saline (0.9%). The lavage fluid was collected using a 14 G catheter into 50 ml plastic conical centrifuge tubes. The guinea pigs were allowed to recover from the anesthesia and could be used again after a two-week rest period.

Cells were isolated from the lavage fluid by centrifugation (400×g, 10 min) and were resuspended in 35 ml of phosphate buffered saline (PBS) and underlayed with 10 ml of isotonic Percoll (1.075 g/ml). This suspension was centrifuged for 30 min at 300×g. The pellet containing mainly eosinophils and erythrocytes was washed in PBS and the erythrocytes lysed. These cells were resuspended in RPMI 1640 medium with 20% FBS and incubated overnight at 37° C. in a humidified 5% $CO_2$ incubator. The next day cells were washed and resuspended in PBS for determination of cell viability (trypan blue exclusion) and purity.

Superoxide Anion Production ($O_2^-$)

Purified eosinophils (viability>95% and purity>90%) were resuspended in PBS with 20 mM HEPES Buffer (pH 7.4) and 0.1 gelatin at a concentration 1–2×10$^6$ cell/ml. Eosinophils (1×10$^5$) were added to a 96 well plate and were incubated for approximately 1 hr at 37° C. PDE 4 inhibitors were added for 10 min prior to the start of the reaction. The reaction was initiated by the addition of cytochrome C (160 $\mu$M) and formylMet-Leu-Phe (fMLP) (30 nM) in the absence or presence of 60 units of superoxide dismutase (SOD). Cytochrome C reduction was monitored on a Dynatech MR 7000 plate reader at 550 nm with a 630 nm reference at various time periods. The rate of $O_2^-$ production was determined by linear regression analysis using the net absorbance of wells in the absence or presence of SOD at several time points. Results were expressed as a percent of the control production of $O_2^-$ corrected for basal release. Sine the maximal inhibition observed was 60%, log $IC_{30}$ were calculated using linear interpolation of the concentration and bracketing 30%.

Example 5—Bronchoconstriction in Guinea Pigs

Male Hartley guinea pigs (200–250 g/4 weeks, Hazelton Research, Denver, Pa.) were sensitized by I.M. injections of 0.35 ml of a 5% (w/v) ovalbumin/saline solution into each thigh (0.7 ml total) on Days 1 and 4. Guinea pigs were available for use after day 25.

Experimental Procedure

Male Hartley guinea pigs (600–800 g Hazelton), actively sensitized to ovalbumin, were anesthetized with sodium pentobarbital (40 mg/kg I.P.) approximately 10–15 minutes prior to surgery. The jugular vein, carotid artery, and trachea were cannulated (Deseret Intracath® Vialon® polymer resin radiopaque catheters (Deseret Medical, Inc., Sandy, Utah), 22 GA and 19 GA, and PE tubing 260, respectively) for drug administration, blood pressure monitoring and ventilation. Bilateral vagotomy was performed to minimize cholinergic interference. Animals were paralyzed (pancuronium bromide, 0.1 mg/kg i.v.) and ventilated (45 breaths/min) via a Harvard Rodent Respirator (model 683, Harvard Apparatus, South Natick, Mass.). Airway pressure changes were measured via a side-arm of the tracheal cannula with a Elcomatic transducer (Buxco Electronics, Sharon, Conn.). The ventilatory stroke volume was set to produce a side arm pressure of 8 cm of $H_2O$ (ca 5 cc room air). Blood pressure was measured with a Statham P23XL Physical Pressure Transducer (Viggo-Spectramed, Oxnard, Calif.). Pressures were recorded on a Grass Model 7D Polygraph (Grass Instrument Co., Quincy, Mass.). The animals were kept warm on a heating table throughout the experiment to maintain body temperature.

Test compounds or vehicle were administered via the i.v. route 10 minutes prior to antigen challenge. At the 0 time point, 0.1 mg/kg ovalbumin is administered via the i.v. route. At the peak of the antigen response, an additional dose of antigen, 0.2 mg/kg ovalbumin, i.v. was administered. After the peak antigen response to the cumulative 0.3 mg/kg ovalbumin was reached, a saturated KCl solution, 1 cc/kg, i.v., was administered which produced maximal bronchoconstriction.

EXAMPLE 6—INHIBITION OF LPS-INDUCED TNFα in Human Monocytes In Vitro Studies To determine whether TNFα inhibition is related to inhibition of LPDE 4 or HPDE 4, a series of PDE 4 inhibitors having a range of potencies for the LPDE 4 and HPDE 4 were screened for their ability to inhibit TNFα production in human monocytes stimulated with lipopolysaccharides (LPS) in vitro. The use of primary human cells for this screen was deemed to be extremely important given that different species appear to differ dramatically in the relative contribution of LPDE 4 and HPDE 4 to cAMP hydrolysis in inflammatory cells.

Methods

TNFα inhibition was assessed in human peripheral blood monocytes which were purified (Collata) from freshly obtained buffy coats or plasma-phoresis residues of blood from normal human donors. Monocytes were plated at density of 1×10$^6$ cells/ml medium/well in 24-well multidishes. The cells were allowed to adhere for 1 hr, after which time the supernatant was aspirated and 1 ml of fresh medium (RPMI-1640 containing 1% fetal calf serum and penicillin/streptomycin at 10 U/ml) was added. The cells were incubated for 45 min in the presence or absence of test compounds at concentrations ranging from 1 nM to 1 mM prior to the addition of LPS (E. coli. 055:B5, Sigma Chemicals) to yield a final concentration of 100 ng/ml. Test compounds were solubilized and diluted in a 50:50 concentration of dimethylsulfoxide/ethanol, such that the final solvent concentration in monocyte culture medium was 0.5% dimethylsulfoxide and 0.5% ethanol. Culture supernants were removed from the monocytes after 14–16 hr incubation at 37° C./5%$CO_2$, and centrifuged at 100×G to remove cell debris. Cytokine assays were performed either immediately or culture supernatants were stored at –70° C. until assayed.

Levels of TNFα were measured using a ELISA (Winston) employing a murine monoclonal anti-human TNFα antibody (see below) as the capture antibody and a polyclonal rabbit antihuman TNFα as the second antibody. For detection, a peroxidase-conjugated goat anti-rabbit (Boehringer Mannheim, Cat. #605222) was added followed by a substrate for peroxidase (1 mg/ml orthophenylenediamine with 0.1% urea peroxide). TNFα levels in samples were calculated from a standard curve generated with recombinant human TNFα produced in *E. coli*. Monoclonal antibodies to human TNFα were prepared from spleens of BALB/c mice immunized with recombinant human TNFα by a modification of the method of Kohler and Milistein (*Nature*, vo. 256, p495–497, 1975). Polyclonal rabbit antihuman TNFα antibodies were prepared by repeated immunization of New Zealand white rabbits with recombinant human TNFα emulsified in complete Freund's adjuvant.

In Vivo Suppression of Human TNFα Production in an Adontive Peritonitis Model Methods One half unit of heparinized venous whole blood was drawn from healthy volunteers who were not taking any kind of medication. Polymorphonuclear luekocytes were separated by layering the blood on Histopaque-1077 with centrifugation at 800×g for 30 min at 25° C. The lymphocyte/monocyte portion was harvested and washed twice with DPBS (Dulbecco's phosphate buffered saline) without $Ca^{2+}$ and $Mg^{2+}$ at 1000 rpm for 10 min at 25° C. The pellet was resuspended in 5 ml of DPBS without $Ca^{2+}$ and $Mg^{2+}$, layered on 5 ml Percoll solution prepared in RPMI 1640 medium which was devoid of serum at 25° C., and centrifuged at 550×g for 30 min at 25° C. The buoyant layer of monocytes was removed and washed twice with DPBS without $Ca^{2+}$ and $Mg^{2+}$ at 1000 rpm for 10 min at 25° C. The final washed monocyte isolate was suspended at $6-10\times10^6$ cells/ml in DPBS without $Ca^{2+}$ and $Mg^{2+}$ at 25° C. Monocytes were also isolated by the same procedure from Source Leukocytes packs. The monocyte preparations ranged from 65 to 90% monocytes and the viability of the cells was >97% (trypan blue exclusion).

BALB/c male (Charles River Laboratories, Wilmington, Mass.) in groups of 4 or 5, were maintained in a barrier-sustained facility. Mice weighting 18–25 g and of the same age were injected with 0.5 ml of $6-10\times10^6$ monocytes/ml into the peritoneum using light pressure on a syringe with a 23 ga needle so that the monocytes were exposed to minimal shearing forces and stress. Within 2 min of receiving monocytes, the mice were treated with vehicle or compound by oral dosing for 15 min. The animals were then injected intraperitoneally (i.p.) with 0.2 ml of 125 mg/ml of endotoxin (*E. coli*., type W, Difco) dissolved in DPBS without $Ca^{2+}$ and $Mg^{2+}$. Two hr later, the animals were euthanized by carbon dioxide asphyxiation and 1.5 ml of DPBS without $Ca^{2+}$ and $Mg^{2+}$ (4° C.) was injected i.p. The peritoneum was gently massaged and the wash was removed and placed in polyproylene tubes in an ice bath. The samples were clarified by centrifugation (12,500×g for 5 min at 4° C.). The supernatants were decanted into new tubes (may be stored at –20° C.) and assayed for human and mouse TNFα by ELISAs. $ED_{50}$ values were calculated by standard procedures.

Example 7—Human Neutrophils Methods

Isolation and Purification

Neutrophils (PMNs) were isolated from heparinized blood by gradient centrifugation using Ficoll (Histopaque 1077) followed by dextran sedimentation to remove the erythrocytes. Any remaining erythrocytes were lysed with water for 30 sec and isotonicity restored using 10× DB-PBS (w/o $Ca^{2+}$ or $Mg^{2+}$). PMNs were isolated by centrifugation and were washed one additional time with 1× DB-PBS prior to determining cell number and viability (trypan blue dye exclusion). Cell number was adjusted to $0.75-1.5\times10^6$ cells/ml depending on the individual donor.

Degranulation (Release of Myeloperoxidase)

An aliquot (0.1 ml) of the above cell suspension was incubated in Earles Balanced Salt Solution containing 20 mM HEPES buffer (pH=7.4) and 0.1% gelatin in the presence of 5 μg/ml of cytochalasin B for 5 min at 37° C. in a shaking water bath. Cells were pretreated for additional 5 min with various concentrations of selective PDE 4 inhibitors and $PGE_2$ (3–10 nM) prior to addition of fMLP (30 nM). fMLP was added and the incubation continued for an additional 30 min. The reaction was terminated by placement of the samples on ice followed by centrifugation. The supernatant fraction was removed and stored frozen (–30° C.) until assay for myeloperoxidase activity.

Determination of Myveloperoxidase Activity

Myeloperoxidase activity was determined using o-dianisidine as substrate and horseradish peroxidase as a standard. An aliquot (50 μl) of supernatant was incubated with 100 μl of substrate (o-dianisidine, 0.53 mM, $H_2O_2$, 0.147 mM; final concentration) in 50 mM Na Phosphate buffer (pH 6.0). The reaction was terminated by the addition of 50 μL of 4 M $H_2SO_4$. Product formation was determined by measuring absorbance at 410 nm and activity determined by comparison to the standard curve using horseradish peroxidase. Data were expressed as percent of control (amount of myeloperoxidase released in the presence of $PGE_2$ alone). Since the maximal inhibition observed for the majority of compounds was 30%, log ($IC_{15}$) values were calculated using linear interpolation of the concentrations bracketing 15%.

Example 8—Reversal of Reserpine-induced Hypothermia in Mice

Male CF-1 or BALB/c mice were individually isolated in wire cages. The rectal temperature of each mouse was recorded prior to pretreatment with reserpine (10 mg/kg, i.p.). Four hours after reserpine the rectal temperatures were recorded and individual animals were given various doses (orally) of either test compounds, vehicle, or rolipram (10 mg/kg). Rectal temperatures were then recorded every 30 min for 2 hr. The data were expressed as the change in temperature from that observed at four hrs post reserpine (temperatures dropped approximately 10–15° C. below basal levels). Dose-response curves were constructed using temperature changes recorded at 90 or 120 min after treatment. $ED_{50}$ values were determined by probit analysis or linear regression of the means of 6–9 animals. To compare the ability of compounds to reverse reserpine-induced hypothermia with their ability to inhibit low affinity binding or high affinity binding, the $ED_{50}$ and $IC_{50}$ values were expressed as –log (value).

Example 9—Relationship Between Biological Function and Inhibition of PDE 4

To determine if certain biological effects of PDE 4 inhibition were associated with inhibition of either the LPDE 4 or HPDE 4 a comparison between the ability of compounds to produce an effect and the ability of compounds to inhibit LPDE 4 or HPDE 4 was determined using a linear and rank order correlation. These correlations can be influenced by several factors: 1) the stability of compounds; 2) ability of compounds to enter cells; 3) in in vivo studies, the bioavailability of compounds; 4) the correlation values, especially the linear correlation are sensitive to the difference in potencies, the greater the range of potency values the easier it is to measure a significant linear correlation. These caveats were taken into consideration when analyzing and summarizing the correlation between inhibition of LPDE 4 or HPDE 4 and the biological function in the various assay systems.

Using isolated inflammatory cells, suppression of monocyte TNFα production and inhibition of superoxide production in guinea pig eosinophils was better correlated with inhibition of LPDE 4 and not HPDE 4. Furthermore, prevention of antigen-induced bronchoconstriction in vivo was better correlated with inhibition of LPDE 4 than HPDE 4. In this in vivo model, PDE 4 inhibitors appear to act by preventing mast cell degranulation (Underwood et al., in press). However, inhibition of inflammatory cell function was not always associated with inhibition of LPDE 4 because it was found that inhibition of neutrophil degranulation was better correlated with inhibition of HPDE 4 than LPDE 4. Thus it appears that some but not all suppression of inflammatory cell activity was associated with inhibition of LPDE 4. In contrast, enhancement of acid secretion, production of emesis and reversal of resperpine-induced hypothermia (a measure of the psychtropic potential of PDE 4 inhibitors) were better correlated with inhibition of HPDE 4 and not LPDE 4. Thus most of the potential side effects of this class of compounds were associated with inhibition of HPDE 4.

Thus these findings suggest that compounds which preferentially inhibit LPDE 4 will produce beneficial anti-inflammatory effects with reduced potential to elicit unwanted side effects. Thus selecting compounds with an $IC_{50}$ ratio of about 0.1 or greater as regards the $IC_{50}$ for PDE 4 catalytic form which binds rolipram with a high affinity divided by the $IC_{50}$ for PDE 4 catalytic form which binds rolipram with a low affinity (HPDE 4/LPDE 4) should result in an increase in their therapeutic index, i.e., the salutary effect is maximized and the deleterious effect is minimized.

To determine if this selection guide would indeed identify compounds with an improved therapeutic index, three models comparing a therapeutic effect with a side effect were evaluated. These included an in vitro comparison between the ability of compounds to suppress TNFα production from isolated human monocytes with their ability to stimulate acid secretion in isolated rabbit parietal glands and two in vivo comparisons examining the ability of compounds to prevent antigen-induced bronchoconstriction in guinea pigs and the ability to elicit emesis in dogs and the ability of compounds to suppress TNFα production in an adoptive transfer model in mice and their ability to reverse reserpine-induced hypothermia in mice.

PDE 4 inhibitors with a selectivity ratio (HPDE 4/LPDE 4) of equal to or greater than 0.1 showed a marked improvement in their therapeutic index. For example, cis-[4-cyano-4-(3-cyclopentyloxy-4-methoxyphenyl)cyclohexan-1-carboxylate], 2-carbomethoxy-4-cyano-4-(3-cyclopropylmethoxy-4-difluoromethoxyphenyl)cyclohexan-1-one, and cis-[4-cyano-4-(3-cyclopropylmethoxy-4-difluoromethoxyphenyl)cyclohexan-1-ol] all with selecitivy ratio of $\geq 0.1$ demonstrate a 100-fold improvement in their therapeutic index in comparison with the archetypal PDE 4 inhibitor, R-rolipram. Thus, this demonstrates that using the selection guide of HPDE 4 $IC_{50}$/LPDE 4 $IC_{50} \geq 0.1$ identifies compounds with an increased therapeutic index in vitro comparison.

As regards treating COPD, the compound cis-[4-cyano-4-(3-cyclopentyloxy-4-methoxyphenyl)cyclohexan-1-carboxylate] was administered to humans suffering from COPD. These subjects experienced reduced inflammation, bronchodilation and pulmonary neuromodulation.

We claim:

1. A method for the prophylaxis of or for treating COPD in a human by administering to a patient in need thereof a PDE 4-specific inhibitor which preferentially inhibits the PDE 4 catalytic form that binds R-rolipram with a low affinity, which method comprises administering to a subject in need thereof an effective amount of a compound having an $IC_{50}$ ratio of about 0.1 or greater as regards the $IC_{50}$ for a PDE 4 form which binds R-rolipram with a high affinity divided by the $IC_{50}$ for the catalytic form which binds R-rolipram with a low affinity, excluding cis-[4-cyano-4-(3-cyclopentyloxy-4-methoxyphenyl)cyclohexan-1-carboxylate].

2. The method of claim 1 wherein the inhibitor has an $IC_{50}$ ratio of about 0.1 or greater as regards the ratio of the $IC_{50}$ value for competing with the binding of 1 nM of [$^3$H]R-rolipram to a form of PDE 4 which binds rolipram with a high affinity over the $IC_{50}$ value for inhibiting the PDE 4 catalytic activity of a form which binds rolipram with a low affinity using 1 μM [$^3$H]-cAMP as the substrate.

3. The method of claim 1 wherein said $IC_{50}$s ratio is 0.5 or greater.

4. The method of claim 1 wherein said $IC_{50}$s ratio is 1.0 or greater.

* * * * *